(12) United States Patent
Dortet et al.

(10) Patent No.: US 9,340,819 B2
(45) Date of Patent: May 17, 2016

(54) METHOD FOR DETECTING THE PRESENCE OF CARBAPENEMASE-PRODUCING BACTERIA IN A SAMPLE

(75) Inventors: Laurent Dortet, Le-Kremlin-Bicetre (FR); Patrice Nordmann, Le-Kremlin-Bicetre (FR); Laurent Poirel, Le-Kremlin-Bicetre (FR)

(73) Assignees: INSERM (INSITUT NATIONAL de la SANTE ET de la RECHERCHE MEDICALE), Paris (FR); ASSISTANCE PUBLIQUE HOPITAUX de PARIS, Paris (FR); UNIVERSITE PARIS SUD (PARIS 11), Paris (FR)

( * ) Notice: Subject to any disclaimer, the term of this patent is extended or adjusted under 35 U.S.C. 154(b) by 0 days.

(21) Appl. No.: 14/128,359

(22) PCT Filed: Jun. 21, 2012

(86) PCT No.: PCT/EP2012/062028
§ 371 (c)(1),
(2), (4) Date: Dec. 20, 2013

(87) PCT Pub. No.: WO2012/175637
PCT Pub. Date: Dec. 27, 2012

(65) Prior Publication Data
US 2014/0134656 A1 May 15, 2014

Related U.S. Application Data

(60) Provisional application No. 61/499,813, filed on Jun. 22, 2011.

(30) Foreign Application Priority Data

Jun. 22, 2011 (EP) .................................... 11305790

(51) Int. Cl.
*C12Q 1/34* (2006.01)
*C12Q 1/04* (2006.01)
(52) U.S. Cl.
CPC ... *C12Q 1/34* (2013.01); *C12Q 1/04* (2013.01)
(58) Field of Classification Search
None
See application file for complete search history.

(56) References Cited

U.S. PATENT DOCUMENTS 6,436,631 B1 * 8/2002 Bochner ........................... 435/4

FOREIGN PATENT DOCUMENTS

WO 2009/051838 A1 4/2009
WO 2010/010083 A1 1/2010

OTHER PUBLICATIONS

Skinner, A., and Wise, R. "A comparison of three rapid methods for the detection of 1-lactamase activity in Haemophilus influenzae", Journal of Clinical Pathology 1977, vol. 30, pp. 1030-1032.*
CHEMnetBASE, "Phenolsulfonphthalein", Dictionary of Organic Compounds; Taylor & Francis Group: Boca Raton, FL; accessed on Apr. 27, 2015.*
A. Tsakris, et al., "Evaluation of Boronic Acid Disk Tests for Differentiating KPC-Possessing klebsiella pneumoniae Isolates in the Clinical Laboratory", Journal of Clinical Microbiology, Feb. 1, 2009, pp. 362-367, vol. 47, No. 2.
Samra Z, et al., "Evaluation of CHROMagar KPC for rapid detection of carbapenem resistant enterobacteriaceae", Journal of Clinical Microbiology, Sep. 1, 2008, pp. 3110-3111, vol. 46, No. 9, American Society for Microbiology, Washington, D.C., US.
Lauretti L, et al., "Cloning and characterization of blaVIM, a new integron-borne metallo-beta-lactamase gene from a Pseudomonas aeruginosa clinical isolate", Antimicrobial Agents and Chemotherapy, Jul. 1, 1999, pp. 1584-1590, vol. 43, No. 7, American Society for Microbiology, Washington, D.C., US.
Queenan Anne Marie, et al., "Carbapenemases: the versatile beta-lactamases", Clinical Microbiology Reviews, Jul. 1, 2007, pp. 440-458, vol. 20, No. 3, Washington, D.C., US.
Philip D. Lister, "Antibacterial resistance", Jan. 1, 2001, pp. 327-365, "Antimicrobial Pharmcodynamics in Theory and Clinical Practice", Mercel Dekker Inc.
Escamilla J, "Susceptibility of Haemophilus influenza to ampicillin as determined by use of a modified, one-minute beta-lactamase test", Antimicrobial Agents and Chemotherapy, Jan. 1976, pp. 196-197, vol. 9, No. 1.
Jain Sarjana, et al., "Rapid detection of extended-spectrum beta-lactamase-producing Gram-negative bacilli in blood cultures", Journal of Antimicrobial Chemotherapy, Sep. 1, 2007, pp. 652-654, Oxford University Press, Great Britain.

* cited by examiner

*Primary Examiner* — Renee Claytor
*Assistant Examiner* — Michelle F Paguio Frising
(74) *Attorney, Agent, or Firm* — Whitham, Curtis, Christofferson & Cook, P.C.

(57) ABSTRACT

The present invention relates to a method for detecting the presence of carbapenemase-producing bacteria in a sample, said method comprising the steps of: a) performing cell lysis on a test sample in order to obtain an enzymatic suspension; b) reacting a fraction of the enzymatic suspension obtained in step a) with a reagent kit, said reagent kit comprising —a carbapenemase substrate selected from the group consisting of carbapenems and cephamycins, —a pH color indicator which will change color when the pH of the reaction mixture is comprised between 6.4 and 8.4, wherein a color change after step b) indicates the presence of carbapenemase-producing bacteria in the test sample. The invention also relates to a reagent kit, to a microtiter plate and to their uses in detecting the presence of carbapenemase producers in a test sample.

13 Claims, 1 Drawing Sheet

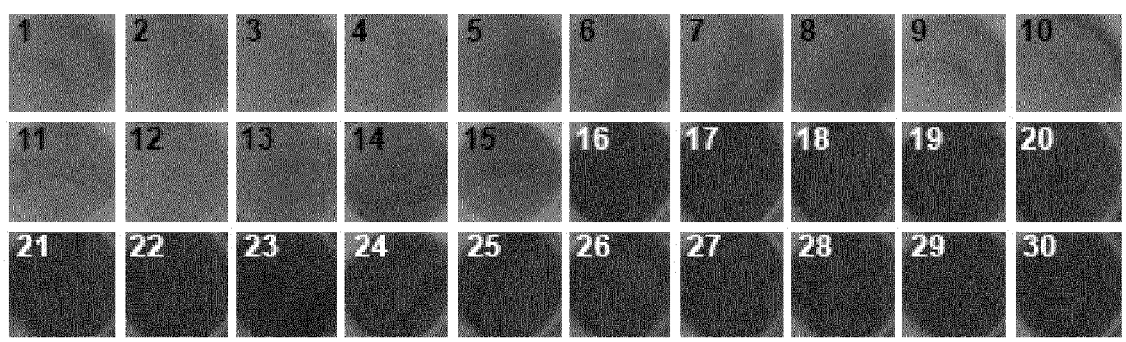

METHOD FOR DETECTING THE PRESENCE OF CARBAPENEMASE-PRODUCING BACTERIA IN A SAMPLE

FIELD OF THE INVENTION

The present invention relates to a method for detecting the presence of carbapenemase-producing bacteria in a sample.

BACKGROUND OF THE INVENTION

Carbapenemase-producing bacteria isolates (i.e. carbapenemase producers) are increasingly identified throughout the world (1-3). Their early detection is becoming a major issue in the field of clinical microbiology in order to prevent their spread and preserve the efficacy of carbapenems which are becoming the antibiotics of last resort for treating severe infections (4). Indeed, carbapenemases are usually associated to many other non-beta-lactam resistant determinants giving rise to multidrug and pandrug resistance. Moreover, due to current population exchange and travel, early recognition of carbapenemase producers is becoming mandatory whatever the antibiotic policy or rate of multidrug-resistant nosocomial infections.

The vast majority of acquired carbapenemases belong to three of the four known classes of beta-lactamases, namely Ambler class A, Ambler class B (metallo-beta-lactamases (MBLs)) and Ambler class D (oxacillinases (OXAs)). These three classes of carbapenemases confer significant clinical resistance to carbapenems or decreased susceptibiility to carbapenems (1-4). Consequently, carbapenemase-producing bacteria isolates from these three classes have been involved both in nosocomial and community-acquired infections.

The spread of the three distinct classes of carbapenemases varies significantly worldwide. For example, KPC producers (Ambler class A) are identified mostly in the Americas and Southern Europe, while IMP, VIM, NDM-1 (Ambler class B) are extensively identified worldwide with a main reservoir for NDM-1 in the Indian subcontinent. As for OXA-48-like enzymes (Ambler class D) are identified at least in the southern and eastern parts of the Mediterranean coast and more recently in Europe (5).

Currently, there exist two types of methods for detecting carbapenemase producers. First, phenotypic-based techniques for in vivo production of carbapenemase such as the "Etest®" and the "Hodge-Test" can be used (4). The "Etest®", is a quantitative technique for determining the antimicrobial susceptibility of many microorganisms. The system comprises a predefined antibiotic gradient which is used to determine the Minimum Inhibitory Concentration (MIC), in µg/mL, of different antimicrobial agents against microorganisms as tested on agar media using overnight incubation. As for the "Hodge-Test", carbapenemase production is detected when the isolate produces the enzyme and allows growth of the carbapenem susceptible strain towards a cabapenem disk. The result of the "Hodge-Test" is a characteristic cloverleaf-like indentation. Unfortunately though, these phenotypic-based techniques are neither sensitive nor specific enough. In many cases also, false-positives have been reported. Alternatively, a molecular detection technique for carbapenemase genes may be used. This technique however remains quite expensive and requires a high degree of expertise. A final drawback of both the phenotypic-based techniques and molecular detection technique is that they are time consuming (12 to 24 h) and therefore do not fulfil clinical requirements requested to implement preventive isolation measures for avoiding development of nosocomial outbreaks (4).

Previous works have performed beta-lactamase identification using a chromogenic cephalosporin such as nitrocefin and CENTA (6, 7). However, these chromogenic substrate molecules cannot specifically detect carbapenemases; they detect any beta-lactamase whatever their hydrolysis profile. As for the Cica-β-test, this test uses the chromogenic cephalosporin HMRZ-86 along with specific inhibitors. Although this test may detect MBL producers, it requires a further culture step. Indeed, the pathogen must first be isolated on an appropriate non-selective medium before being tested. Then, only an isolated colony is used in order to avoid contamination and ensure that the organism is pure. Other tests, such as iodometric tests and acidimetric tests using benzylpenicillin as substrates have been used, but are also not specific for the detection of carbapenemases (6). Finally, techniques using imipenem containing starch agar have also been used to detect MBL activity (8). However, this last technique requires protein extraction, partial beta-lactamase purification, electrophoresis migration as well as an extensive knowledge of the beta-lactamase field. It is therefore time consuming and is usually reserved for research purposes only.

To facilitative the detection of carbapenemases-producers in the field of clinical microbiology, the Applicant has developed a new method based on a simple acido-colorimetric technique. This method is based on the concept that by hydrolysing the beta-lactam ring of a carbapenemase substrate, the carbapenemases generate a carboxyl group which in turn acidifies a medium. The acidity resulting from this hydrolysis is then identified by a color change of a pH color indicator (9).

This method helps differentiate the carbapenemase producers from those that are carbapenem resistant resulting from non-carbapenemase mediated mechanisms such as combined mechanisms of resistance (eg. outer membrane permeability defect, overproduction of cephalosporinases, clavulanic-acid inhibited ESBL . . . ) or from strains expressing broad-spectrum β-lactamases without carbapenemase activity (ESBLs, plasmid and chromosome-encoded cephalosporinases) (10).

Interpretable results are obtained within a very short time, which is crucial when designing containment measures for carbapenemase producers. It eliminates the need of using the "Etest®" or "Hodge-Test" technique which, as mentioned previously, is neither specific nor sensitive and which needs an additional 18 h before obtaining interpretable results.

This method offers a solution for fast, reliable and affordable detection of any type of carbapenemases-producers. In addition, it is specific and sensitive. It may also be submitted to an industrialization process such that it may be implemented in any clinical microbiology laboratory worldwide without significant additional workload for laboratory technicians.

Moreover, in the field of epidemiology, the use of this method may be of further help when wanting to rapidly select strains which should be tested by PCR and sequenced for identification of carbapenemase genes.

SUMMARY OF THE INVENTION

The present invention relates to a method for detecting the presence of carbapenemase-producing bacteria in a sample, said method comprising the steps of:
a) performing cell lysis on a test sample in order to obtain an enzymatic suspension;

b) reacting a fraction of the enzymatic suspension obtained in step a) with a reagent kit, said reagent kit comprising
    a carbapenemase substrate selected from the group consisting of carbapenems and cephamycins,
    a pH color indicator which will change color when the pH of the reaction mixture is comprised between 6.4 and 8.4
wherein a color change after step b) indicates the presence of carbapenemase-producing bacteria in the test sample.

The present invention also relates to a reagent kit comprising a carbapenemase substrate selected from the group consisting of carbapenems and cephamycins and a pH color indicator and its use in detecting the presence of carbapenemase producers in a test sample.

The invention also relates to a microtiter plate comprising a well or a series of wells comprising a carbapenemase substrate selected from the group consisting of carbapenems and cephamycins, its use in detecting the presence of carbapenemase producers in a test sample and it use in eventually determining the specific class of carbapenemase present in a test sample.

DETAILED DESCRIPTION OF THE INVENTION

Definitions

As used herein, "test sample" means any liquid or solid material to be tested which may contain carbapenemase-producing bacteria. Typically, a bacterial colony may be isolated from such a material. The preferred "test sample" is a biological sample.

As used herein, "biological sample" means any biological sample obtained from a subject. Examples of such "biological samples" include fluids, tissues, cell samples, etc. Preferred "biological samples" are whole blood, serum, plasma or urine.

As used herein, "subject" denotes a mammal, such as a rodent, a feline, a canine, and a primate. Preferably a "subject" according to the invention is a human.

As used herein, "pH color indicator" is a halochromic chemical compound that is added in small amounts to a solution so that the pH of the solution/medium can be determined visually. The indicator causes the color of the solution/medium to change depending on the pH.

As used herein, "enzymatic suspension" means that the step of cell lysis (step a) of the method according to the invention) helps liberate enzymes which are present within the cells of the test sample, thereby obtaining an "enzymatic suspension".

As used herein, "fraction" means that all or part of the enzymatic suspension obtained in step a) of the method according to the invention is taken in order to be reacted with the reagent kit in step b). Typically, a "fraction" according to the invention is a part of the enzymatic suspension. Preferably, a "fraction" according to the invention is 10 µL to 50 µL.

As used herein, a "kit" means a product comprising a number of different components, as a combination product, for separate, simultaneous or sequential use in the method of the invention. Preferably, the components are a carbapenemase substrate selected from the group consisting of carbapenems and cephamycins, a pH color indicator, optionally a carbapenemase activator and optionally a carbapenemase inhibitor.

Detection Method:

As previously mentioned, early detection of carbapenemase-producing bacteria is becoming a major issue in the field of clinical microbiology in order to prevent their spread and preserve the efficacy of carbapenems which are becoming the antibiotics of last resort for treating severe infections.

As a solution to this problem, the Applicant has developed a fast, reliable and affordable method for detecting any type of carbapenemases producers.

The present invention therefore relates to a method for detecting the presence of carbapenemase-producing bacteria in a sample, said method comprising the steps of:
a) performing cell lysis on a test sample in order to obtain an enzymatic suspension;
b) reacting a fraction of the enzymatic suspension obtained in step a) with a reagent kit, said reagent kit comprising
    a carbapenemase substrate selected from the group consisting of carbapenems and cephamycins,
    a pH color indicator which will change color when the pH of the reaction mixture is comprised between 6.4 and 8.4,
wherein a color change after step b) indicates the presence of carbapenemase-producing bacteria in the test sample.

The method of the invention is based on the concept that by hydrolysing the beta-lactam ring of a carbapenemase substrate, the carbapenemases generate a carboxyl group which in turn acidifies a medium, typically an unbuffered medium. The acidity resulting from this hydrolysis is then identified by a color change of a pH color indicator. A change in color indicates the presence of a carbapenemase.

Typically, a broth is inoculated with a test strain (obtained from a test sample) and incubated on a rotative shaker. Then, the culture is centrifuged and the pellet resuspended in a lysis buffer, vortexed and further incubated (similarly, a direct lysis protocol, known to the skilled person in the art, can be applied using bacterial colonies grown on solid culture medium). After sufficient incubation, the suspension (i.e. enzymatic suspension) is centrifuged and the supernatant is removed and placed on ice. A small fraction of this supernatant is mixed with a reagent kit comprising a carbapenemase substrate and a pH color indicator. The mixture composed of the reagent kit and the tested enzymatic suspension is further incubated at a temperature and for a sufficient amount of time such that a change of color is observed. A change of color indicates the presence of a carbapenemase. The color change may be obtained as early as 5 minutes after starting the incubation. In most cases, a 30 minutes incubation time is sufficient for obtaining a frank color change for carbapenemase producers.

Typically, the use of this method may be of further help when wanting to rapidly select strains which should be tested by PCR and sequenced for identification of carbapenemase genes. Consequently, once the presence of carbapenemase producers has been determined by the present method, other identification techniques known to the skilled person in the art may be used to further characterize the carbapenemase and/or carbapenemase producers.

Typically, once a carbapenemase activity has been detected by the method of the invention, this carbapenemase activity may be further used to discover or evaluate novel carbapenemase inhibitors or novel molecules resistant to the activity of the carbapenemase. In the latter case, the novel molecule to be evaluated may replace the carbapenemase substrate molecule contained in the reagent kit.

Typically, the method according to the present invention may be used to detect any carbapenemase-producing bacteria selected from the group consisting of gram positive and gram negative bacteria. Preferably, the carbapenemase-producing bacteria are selected from the group consisting of bacteria which are of clinical importance and even more preferably from the group consisting of gram negative bacteria which are of clinical importance.

As used herein, bacteria of "clinical importance" means bacteria involved in nosocomial and community-acquired infections.

Typically, the carbapenemase-producing bacteria are selected from the genera consisting of *Acinetobacter, Aeromonas, Bacillus, Bacteroides, Citrobacter, Enterobacter, Escherichia, Klebsiella, Morganella, Pandoreae, Proteus, Providencia, Pseudomonas, Ralstonia, Raoultella, Salmonella, Serratia, Shewanella, Shigella* and *Strenotrophomonas*.

Typically, the carbapenemase-producing bacteria are selected from the group consisting of *Acinetobacter baumannii, Aeromonas junii, Bacillus cereus, Bacteroides fragilis, Citrobacter amalonaticus, Citrobacter freundii, Citrobacter youngae, Enterobacter aerogenes, Enterobacter asburiae, Enterobacter cloacae, Escherichia coli, Klebsiella oxytoca, Klebsiella pneumoniae, Morganella morganii, Pandoraea pnomenusa, Proteus mirabilis, Proteus rettgeri, Proteus vulgaris, Providencia stuartii, Pseudomonas aeruginosa, Salmonella enterica, Serratia marcescens, Shigella flexneri, Stenotrophomonas maltophilia, Ralstonia picketti* and *Shewanella algae*.

Typically, the Ambler Class A carbapenemase-producing bacteria are selected from the group consisting of the species *Citrobacter freundii, Enterobacter aerogenes, Enterobacter asburiae, Enterobacter cloacae, Escherichia coli, Klebsiella oxytoca, Klebsiella pneumoniae, Pseudomonas aeruginosa, Salmonella enterica* and *Serratia marcescens*, the Ambler Class B carbapenemase-producing bacteria are selected from the group consisting of the species *Acinetobacter baumannii, Aeromonas junii, Bacillus cereus, Bacteroides fragilis, Citrobacter amalonaticus, Citrobacter freundii, Citrobacter youngae, Enterobacter aerogenes, Enterobacter cloacae, Escherichia coli, Klebsiella oxytoca, Klebsiella pneumoniae, Morganella morganii, Proteus rettgeri, Proteus vulgaris, Providencia stuartii, Pseudomonas aeruginosa, Serratia marcescens, Shigella flexneri* and *Stenotrophomonas maltophilia*, and the Ambler Class D carbapenemase-producing bacteria are selected from the group consisting of the species *Acinetobacter baumannii, Escherichia coli, Klebsiella pneumoniae, Pandoraea pnomenusa, Pseudomonas aeruginosa, Ralstonia picketti* and *Shewanella algae*.

According to the present invention, the carbapenemase-producing bacteria are preferably selected from the genera consisting of *Acinetobacter, Enterobacter, Escherichia, Klebsiella, Pseudomonas* and *Shewanella*, and even more preferably selected from the group consisting of *Acinetobacter baumannii, Escherichia coli, Klebsiella pneumoniae* and *Pseudomonas aeruginosa*.

As used herein according to the present invention, a carbapenemase substrate is one which is selected from the group consisting of carbapenems and cephamycins.

Typically, the carbapenem is selected from the group consisting of biapenem, ertapenem, doripenem, imipenem, meropenem, tebipenem and panipenem.

Typically, the cephamycin is selected from the group consisting of moxalactam and cefoxitin. Cephamycins are particularly interesting for the detection of carbapenemases of Ambler Class B (11).

Preferably, the carbapenemase substrate is imipenem.

Typically, the concentration of carbapenemase substrate used in the reagent kit is comprised between 0.1 mg/ml and 10 mg/ml, more preferably between 1 mg/ml and 5 mg/ml and even more preferably between 2 mg/ml and 3 mg/ml.

According to the invention, the pH color indicator will change color when the pH of the reaction mixture is comprised between 6.4 and 8.4, preferably between 6.6 and 7.5.

Typically, the concentration of pH color indicator used in the reagent kit is comprised between 0.01% and 1%, more preferably between 0.03% and 0.08% and even more preferably between 0.05% and 0.06%.

Typically, the skilled person in the art is able to select a proper pH color indicator for this hydrolysis reaction. A list of pH indicators which may be used in the present invention can be found in the CRC Handbook of Chemistry and Physics: A Ready-reference Book of Chemical and Physical Data, 91$^{st}$ Revised ed. (Jun. 1, 2010), CRC Press Inc. For example, the pH color indicator used in the present invention may be selected from the group consisting of 6,8-dinitro-2,4-(1H) quinazolinedione (pH: 6.4 to 8.0), bright yellow (pH: 6.6 to 7.8), phenol red (pH: 6.6 to 8.0) and neutral red (pH: 6.8 to 8.0).

Preferably, the pH color indicator used in the present invention is phenol red and when it is used a color change from red to yellow indicates the presence of carbapenemase-producing bacteria in the test sample.

Typically, the reaction in step b) is carried out over a period of time sufficient to observe a color change. Preferably, the color change is visually observed within a time period comprised between 5 minutes and 120 minutes, preferably between 10 and 60 minutes, more preferably between 20 and 40 minutes. Alternatively, identification of the color change may be automatised by using a photometer for example.

Typically, the reaction in step b) is carried out at a temperature comprised between 15° C. and 40° C., preferably between 20° C. and 37° C., more preferably between 35° C. and 37° C.

Based on molecular studies, carbapenemases can be further divided into two types: serine enzymes possessing a serine moiety at the active site (Ambler Class B, C, and D), and MBLs (Ambler Class B) which require divalent cations, usually zinc, as metal cofactors for enzyme activity, thereby facilitating hydrolysis of the bicyclic beta-lactam ring (12).

Thus, according to a further embodiment of the invention, in order to increase the sensitivity of the method, the reagent kit further comprises a carbapenemase activator, which is selected from the group consisting of divalent cations or salts thereof, and mixtures thereof.

Typically, in the case of carbapenemases of Ambler class B, the activator is a divalent cation or salt thereof selected from the group consisting of manganese, cobalt, nickel, cadmium, mercury, zinc and mixtures thereof (see Biochem J. 1974; 143(1):129-35 and the Journal of Biological Chemistry vol. 285, NO. 7, 4570-4577). Preferably, the carbapenemase activator is zinc.

Typically, the concentration of carbapenemase activator present in the reagent kit is comprised between 0.01 mM and 1 mM, more preferably between 0.05 mM and 0.5 mM and even more preferably between 0.08 mM and 0.12 mM.

Typically, a broth is inoculated with a test strain (obtained from a test sample) and incubated on a rotative shaker. Then, the culture is centrifuged and the pellet resuspended in a lysis buffer, vortexed and further incubated. After sufficient incubation, the suspension (i.e. enzymatic suspension) is centrifuged and the supernatant is removed and placed on ice. A small fraction of this supernatant is mixed with a reagent kit comprising a carbapenemase substrate, a pH color indicator and a carbapenemase activator. The mixture composed of the reagent kit and the tested enzymatic suspension is further incubated at a temperature and for a sufficient amount of time such that a change of color is observed. A change of color indicates the presence of a carbapenemase. The color change may be obtained as early as 5 minutes after starting the incubation. In most cases, a 30 minutes incubation time is sufficient for obtaining a frank color change for carbapenemase producers.

In a preferred embodiment, there is provided a method for detecting the presence of carbapenemase-producing bacteria in a biological sample, said method comprising the steps of:
a) performing cell lysis on a biological sample in order to obtain an enzymatic suspension;
b) reacting a fraction of the enzymatic suspension obtained in step a) with a reagent kit, said reagent kit comprising
  imipenem as the carbapenemase substrate,
  phenol red as the pH color indicator, and
  zinc or salt thereof as the carbapenemase activator,
wherein a color change from red to yellow after step b) indicates the presence of carbapenemase-producing bacteria in the biological sample.

According to an embodiment, in order to specifically identify the class of carbapenemase which is present in the test sample, whether an Ambler Class A, B or D carbapenemase, a carbapenemase inhibitor may be used.

Typically, the carbapenemase inhibitor may be mono-specific for one class of carbapenemase. For example, carbapenemase inhibitors are selected from the group consisting of clavulanic acid, tazobactam, sulbactam, and aminophenylboronic acid for carbapenemases of Ambler class A, and selected from the group consisting of 1-10 phenanthroline, dipicolinic acid, thiols compounds (such as mercaptopropionic acid and mercaptoacetic acid) and EDTA for carbapenemases of Ambler class B (12-17).

In a preferred embodiment, the mono-specific carbapenemase inhibitor for carbapenemases of Ambler class A is tazobactam.

In a preferred embodiment, the mono-specific carbapenemase inhibitor for carbapenemases of Ambler class B is EDTA, more preferably EDTA associated with a depletion of $ZnSO_4$. Indeed, the activity of EDTA is enhanced by a depletion of divalent cations.

Typically, the carbapenemase inhibitor may be bi-specific for more than one class of carbapenemase, such as for example NXL-104 which is bi-specific for carbapenemases of Ambler classes A and D (12-17).

Typically, the concentration of mono-specific carbapenemase inhibitor for carbapenemases of Ambler class A (such as for example tazobactam) is comprised between 0.1 mg/ml and 10 mg/ml, more preferably between 1 mg/ml and 5 mg/ml and even more preferably between 2 mg/ml and 3 mg/ml.

Typically, the concentration of mono-specific carbapenemase inhibitor for carbapenemases of Ambler class B (such as for example EDTA) is comprised between 0.001 M and 0.5 M, more preferably between 0.001 M and 0.01 M and even more preferably at 0.005 M.

Typically, the concentration of bi-specific carbapenemase inhibitor for carbapenemases of Ambler classes A and D (such as for example NXL-104) is comprised between 0.05 mg/ml and 10 mg/ml, more preferably between 1 mg/ml and 8 mg/ml and even more preferably between 3 mg/L and 5 mg/ml.

Typically, in order to identify the class of carbapenemase, one may use a 96-well microtiter plate and divide the plate in four sections. In a first section, the presence of carbapenemases may be detected according to the method of the invention as described previously. In a second section, carbapenemases of Ambler class A may be detected by adding a carbapenemase inhibitor for carbapenemases of classes A. In a third section, carbapenemases of Ambler class B may be detected by adding a carbapenemase inhibitor for carbapenemases of classes B (eventually with a $ZnSO_4$ depletion).

Finally, in a fourth section, carbapenemases of Ambler class D may be detected by adding a carbapenemase inhibitor for carbapenemases of class D. Depending on the carbapenemase inhibitor used, the skilled person in the art is then able, by simple deduction, to establish the specific Ambler class(es) of carbapenemase which is(are) present in the test sample.

Typically, the carbapenemase inhibitor may be part of the reagent kit itself and thus added at the same time as the carbapenemase substrate, the pH color indicator and optionally the carbapenemase activator.

Alternatively, the carbapenemase inhibitor may be separate from the reagent kit and thus added simultaneously or sequentially to the reagent kit and/or the test sample (fraction of the enzymatic suspension).

Once, the method according to the invention has been performed in all of the four sections, that is, with or without the carbapanemase inhibitors, a comparison is established between results obtained after performing the method as described above and results obtained after performing the same method in which a carbapenemase inhibitor was further added.

Reagent Kit:

According to another aspect of the invention, there is provided a reagent kit comprising a carbapenemase substrate selected from the group consisting of carbapenems and cephamycins and a pH color indicator.

According to an embodiment of the invention, the reagent kit may further comprise a carbapenemase activator. Thus, the reagent kit may comprise a carbapenemase substrate, a pH color indicator and a carbapenemase activator.

According to an embodiment of the invention, the reagent kit may further comprise a carbapenemase inhibitor. Thus, the reagent kit may comprise a carbapenemase substrate, a pH color indicator, a carbapenemase activator and a carbapenemase inhibitor.

The carbapenemase substrate, pH color indicator, carbapenemase activator and carbapenemase inhibitor are as defined previously in the present patent application.

Typically, the reagent kit is used to detect the presence of carbapenemase-producing bacteria in a sample according to the method of the present invention.

Typically, when the specific carbapenemase inhibitor is present in the reagent kit, the corresponding specific class of carbapenemases, whether Ambler class A, B or D, may be determined.

Microtiter Plate:

According to another aspect of the invention, there is provided a microtiter plate comprising a well or a series of wells comprising a carbapenemase substrate selected from the group consisting of carbapenems and cephamycins.

Typically, the microtiter plate may further comprise:
  a well or a series of wells which comprise a carbapenemase substrate selected from the group consisting of carbapenems and cephamycins and a carbapenemase inhibitor of Ambler class A;
  a well or a series of wells which comprise a carbapenemase substrate selected from the group consisting of carbapenems and cephamycins and a carbapenemase inhibitor of Ambler class B (eventually with a $ZnSO_4$ depletion); and
  a well or a series of wells which comprise a carbapenemase substrate selected from the group consisting of carbapenems and cephamycins and a carbapenemase inhibitor of Ambler class D.

The microtiter plate may also contain a control well or a series of control wells which can be assayed and compared to the test samples.

Typically, the microtiter plate is a 96-well microtiter plate.

Devices other than microtiter plates may be used for this purpose. For example, a blotting paper in which the reagent kit (i.e. the carbapenemase substrate and the pH color indicator) has been incorporated may be used. Upon addition of the enzymatic suspension to the blotting paper, one can observe whether the paper changes color or not. Similarly, plastic galleries may be used. Indeed, the reagent kit may be included in these plastic galleries and then, upon addition of the enzymatic suspension into these galleries, one can observe whether there is a color change or not.

In order for the method of the invention to be performed, a pH color indicator, an optional carbapenamase activator and a fraction of the enzymatic suspension to be tested are added to each well of the microtiter plate. Consequently, there is provided the use of a microtiter plate for detecting the presence of carbapenemase-producing bacteria in a test sample according to the method of the present invention, whereby to each well is added at least a pH color indicator and a fraction of the enzymatic suspension to be tested. The microtiter plate is particularly well suited to determine the specific class of carbapenemase present in a test sample.

Typically, if the pH color indicator is stable, the well or series of wells of the microtiter plate may also comprise the pH color indicator with the carbapenemase substrate or with the carbapenemase substrate and the carbapenemase inhibitor prior to performing the method of the invention. Alternatively, if the pH color indicator is not stable, it may be added to the well or series of wells afterwards.

Typically, a carbapenemase activator may also be added to the well or series of wells of the microtiter plate with the carbapenemase substrate or with the carbapenemase substrate and the carbapenemase inhibitor prior to performing the method of the invention. Alternatively, a carbapenemase may be added to the well or series of wells afterwards.

The carbapenemase substrate, the pH color indicator, the carbapenemase activator and the carbapenemase inhibitor are as defined previously in the present patent application.

According to an embodiment, some of the components such as for example the carbapenemase substrate and the carbapenemase inhibitor (when present), may be directly bound to a solid surface of the microtiter plate. In this case, the remaining components (i.e. the pH color indicator and the optional carbapenemase activator) are added to the surface-bound carbapenemase substrate and to the surface-bound carbapenemase inhibitor (when present) in the microtiter plate with the test sample.

According to an embodiment, the microtiter plate as well as each of the elements used to perform the method of the invention may be enclosed within an individual container and all of the various containers may be placed within a single package along with instructions for observing whether carbapenemase-producing bacteria can be found in the test sample.

The invention will further be illustrated in view of the following FIGURE and examples.

FIGURE

FIG. 1. Results for the method of detection of carbapenemase producers.

Carbapenemase producers (darkened numbers) are as follows: E. cloacae KPC-2 (1), E. coli COL KPC-2 (2), K. pneumoniae H1516-6 COL KPC-2 (3), K. pneumoniae BIC OXA-48 (4), K. pneumoniae CHA OXA-48 (5), E. cloacae TUR OXA-48 (6), E. coli HAN OXA-48 (7), K. pneumoniae OMA OXA-181 (8), P. rettgeri RAP OXA-181 (9), K. pneumoniae UK NDM-1 (10), K. pneumoniae 1 OMA NDM-1 (11), E. coli 271 AUS NDM-1 (12), C. freundii STE NDM-1 (13), E. coli MAD VIM-1 (14), K. pneumoniae MAD IMP-13 (15).

No carbapenemase producers are (whitened numbers) as follows: K. pneumoniae CTX-M-15 (16), E. cloacae CTX-M-15 (17), E. coli CTX-M-14 (18), K. pneumoniae 6299 OXA-163 (19), E. coli VEB-1 (20), E. coli ACC-1 (21), K. pneumoniae DHA-2 (22), E. coli Ec13 SYD CMY-2 (23), E. coli VMC CMY-10 (24), E. cloacae ARF overexpressed AmpC (25), E. cloacae CON overexpressed AmpC (26), K. pneumoniae COO porin deficiency (27), K. pneumoniae BER porin deficiency (28), E. coli J53 wild-type (29), K. pneumoniae CIP53153 wild-type (30).

EXAMPLES

Example 1

Method (Acido-Colorimetric Test) According to the Invention

Thirty six carbapenemase-producing isolates of various enterobacterial species of the Applicant's own strain collection and of worldwide origin were included in the study (Table 1). These strains had been previously characterized for their beta-lactamases content at the molecular level.

The collection of strains also contained a series of isolates with decreased susceptibility to carbapenems by non-carbapenemase based mechanisms or by producing non-carbapenemase broad spectrum beta-lactamases frequently identified among clinical isolates (Table 2).

Prior to performing the method of the invention, susceptibility testings were performed by determining Minimum Inhibitory Concentration (MIC) values by the Etest® (AB bioMérieux; Solna, Sweden) on Mueller-Hinton agar plates at 37° C. and results of susceptibility testing were recorded according to the Clinical and Laboratory Standards Institute (CLSI) guidelines as modified in June 2010 (18). The breakpoints for imipenem are S≤1 µg/ml (susceptibility) and R≥4 µg/ml (resistant). As for those for ertapenem, they are S≤0.25 µg/ml and R≥1 µg/ml (see Tables 1 and 2).

The strains were submitted to the method of the present invention as follows.

10 ml of trypticase soy broth were inoculated with two colonies of the test strain and incubated for 3 h at 37° C. on a rotative shaker. Then, the culture was centrifuged at 10,000 g at 4° C. for 15 min. The pellet was resuspended in Tris-HCL 20 mM lysis buffer (B-PERII, Bacterial Protein Extraction Reagent, Thermo Scientific, Pierce), vortexed for 1 min and further incubated at room temperature for 30 min. For obtaining an high quality protein extraction from blood cultures, bacterial pellet is resuspended in lysis buffer (B-PERII, Bacterial Protein Extraction Reagent, ThermoScientific Pierce) and then transferred in MicroBead tubes (Ultraclean bacterial DNA isolation kit Bead tubes (MO BIO laboratories) and mechanical lysis of bacteria is obtained by strong agitation of Microbead tubes using a vortex adaptater for 30 min at room temperature This bacterial suspension was centrifuged at 10,000 g at 4° C. for 5 min. and the supernatants were removed and placed on ice. 30 µl of this suspension supernatants (i.e. enzymatic suspension) were mixed in a well of a 96 well tray with 100 µl of a 1 ml solution made of 3 mg imipenem monohydrate, phenol red solution pH 7.5 and $ZnSO_4$ 0.1 mM (i.e. the reagent kit).

The phenol red solution used by the Applicant was made by taking 2.2 ml of a concentrated phenol solution pH 8 (made from a mixture of phenol red 0.5% in distilled water) to which Applicant added 16.6 ml distilled water. The pH value was then adjusted to 7.5 by adding drops of 1 N NaOH solution.

Mixtures of the reagent kit and tested enzymatic suspension were incubated at 37° C. for 1 h. Suspensions of bacterial strains producing or not carbapenemases (positive and negative controls) were also tested according to the method of the invention. The color of the wells turn from red to yellow for all tested strains producing any type of carbapenemases whereas wells corresponding to bacterial extracts of isolates that did not produce carbapenemases remained red whatever the level of susceptibility to carbapenems was (FIG. 1. See also Tables 1 and 2 for the results). The color change from red to yellow was obtained as early as 5 min after the incubation start for KPC producers. In most of the cases, a 30 min incubation time was sufficient for obtaining a frank color change for carbapenemase producers. The color change although still positive was less frank with several isolates such as several IMP and VIM producers. The testing was conducted as a blind study by a person who did not know which well comprised the carbapenemase producers. All tests were performed in triplicate with highly reproducible results.

Example 2

Rapid Detection of Carbapenemase-Producing Enterobacteriaceae

Abstract

The Carba NP test was developed for a rapid identification of any carbapenemase producer in Enterobacteriaceae. This biochemical test using isolated bacterial colonies is based on in-vitro hydrolysis of a carbapenem, imipenem. It was 100% sensitive and specific as compared to molecular-based techniques. This rapid (less than 2 h) and inexpensive technique may be implemented in any laboratory. It constitutes a real change of the paradigm for controlling the spread of carbapenemase producers worldwide.

Study

One hundred sixty-two carbapenemase-producing strains of various enterobacterial species isolated from various clinical samples (blood cultures, urine, sputum, . . . ) from our own strain collection and of global origin, were included in the study (Table 3). This collection of strains also included forty-six strains being fully susceptible to carbapenems or showing a decreased susceptibility to carbapenems as a consequence of non-carbapenemase-based mechanisms (Table 4). Antibiograms were done for all strains on Mueller-Hinton agar (Biorad, Marnes-la-Coquette, France) according to CLSI guidelines (Clinical and Laboratory Standards Institute. Performance Standards for Antimicrobial Susceptibility Testing; Twenty-Second Informational Supplement. M100-S22. Wayne (PA), USA: CLSI; 2012). The Carba NP (Carbapenemase Nordmann-Poirel) test was performed as follows. One calibrated dose (10 µl) of the tested strain directly recovered from the antibiogram was re-suspended in a Tris-HCl 20 mM lysis buffer (B-PERII, Bacterial Protein Extraction Reagent, Thermo Scientific, Pierce), vortexed for 1 min and further incubated at room temperature for 30 min. This bacterial suspension was centrifuged at 10,000×g at room temperature for 5 min. Thirty µl of the supernatant, corresponding to the enzymatic bacterial suspension, was mixed in a well of a 96 well tray with 100 µl of a 1 ml solution made of 3 mg of imipenem monohydrate (Sigma, Saint-Quentin Fallavier, France) pH 7.8 phenol red solution and 0.1 mM ZnSO4 (Merck Millipore, Guyancourt, France). The phenol red solution used was prepared by taking 2 ml of a phenol red (Merck Millipore) solution 0.5% w/v to which 16.6 ml of distilled water was added. The pH value was then adjusted to 7.8 by adding drops of 1 N NaOH. Mixture of the phenol red solution and the enzymatic suspension being tested was incubated at 37° C. for a maximum of 2 h. Test results were interpreted by technicians who were blinded to the identity of the samples.

All strains had previously been characterized for their β-lactamase content at the molecular level. Minimum inhibitory concentration of carbapenem were determined using the Etest® (AB bioMérieux, Solna, Sweden) and results were recorded according to US guidelines (CLSI), as updated in 2011.

Using the Carba NP test, the color of the wells turned from red to orange or yellow for all tested strains producing carbapenemases (Table 3) whereas wells corresponding to bacterial extracts of isolates that did not produce carbapenemase remained red, whatever their level of carbapenem susceptibility was (Table 4). The color change from red to yellow was obtained as early as 5-10 min after the start of incubation for KPC producers. In most cases, a 30 min incubation was sufficient for obtaining a frank color change for carbapenemase producers. The test's specificity and sensitivity were both at 100% as compared to molecular-based identification of carbapenemase genes taken as a gold standard. All tests were performed in triplicate, giving identical and reproducible results.

The Carba NP test perfectly differentiates carbapenemase producers (Table 3) from strains that were carbapenem resistant due to non-carbapenemase-mediated mechanisms such as combined mechanisms of resistance (outer-membrane permeability defect associated with overproduction of cephalosporinase and/or ESBLs) or from strains that are carbapenem susceptible but expressed a broad-spectrum β-lactamase without carbapenemase activity (ESBL, plasmid and chromosome-encoded cephalosporinases) (Table 4). Interpretable positive results were obtained in less than 2 h total time, which is unique, making it possible to implement rapid containment measures to limit the spread of carbapenemase producers.

Conclusions

The Carba NP test has multiple benefits. It is inexpensive, rapid, reproducible and highly sensitive and specific, eliminating the need for other techniques for identification of carbapenemase producers which are time-consuming and less sensitive or specific. Using this accurate test would significantly improve the detection of patients infected or colonized with carbapenemase producers. The Carba NP test has been routinely implemented in our department and is giving excellent results (data not shown). In addition, it has significantly decreased the lab technicians workload and has simplified the clinical management of potential carbapenemase producers.

This test could be used, for example, for directly testing (i) bacteria obtained from antibiogram of blood culture, and/or (ii) bacterial colonies grown on culture media prior to antibiotic susceptibility testing. For antibiotic stewardship on bacteria isolated directly from those clinical samples, the time gain for detection carbapenemase producers is expected to be at least 24 h. It could also be used for rapid identification of isolates that are resistant to carbapenems and/or to extended-spectrum cephalosporins obtained from screening for multi-drug-resistant bacteria recovered from stools. This would be of utmost importance for preventing outbreaks. The use of the Carba NP test may support novel antibiotic development by facilitating patient enrollment in pivotal clinical trials. This test used as a home brew test may contribute to global surveillance network.

Results from the Carba NP test can efficiently select the strains to be further tested by PCR and/or submitted to sequencing for a detailed identification of the carbapenemase genes. Finally, another area of use of the test could be in low-income countries that are known to be large reservoirs of carbapenemase producers. It offers, for the first time, a friendly solution for detecting one of the main component of the multidrug resistance in Enterobacteriaceae. Use of the Carba NP test will contribute to a better stewarship of carbapenems by changing the paradigm of controlling carbapenemase producers worldwide.

Example 3

Rapid Detection of Carbapenemase-Producing *Pseudomonas* Spp.

Abstract

Carbapenem resistance in *Pseudomonas* spp. is mainly related to decreased outer-membrane permeability, or to expression of carbapenemases. Currently, carbapenemases detection relies on phenotypic- or molecular-based techniques that are either not enough sensitive or specific, or are expensive. In addition, those techniques are time-consuming and therefore of limited clinical interest. A novel technique, the Carba NP test, based on the in-vitro hydrolysis of a carbapenem, has been here evaluated to detect carbapenemase production in *Pseudomonas* spp. It was tested with 36 carbapenemase and 72 non-carbapenemase producers. The Carba NP test was specific and sensitive (100% and 94.4%, respectively), and rapid (less than 2 h). This cost-effective technique can be implemented in any clinical microbiology laboratory worldwide. It offers a reliable technique for identification of carbapenemase-producing *Pseudomonas* spp., and therefore a very useful tool for preventing their nosocomial spread.

Methods

Strains Collection

Thirty-six carbapenemase-producing isolates belonging to several *Pseudomonas* species, isolated from various clinical samples (blood cultures, urine, sputum, etc. . . . ) from our strain collection and being of global origin have been included in this study (Table 5). The strains had been previously characterized for their β-lactamase content at the molecular level. This collection also contained 72 strains being representative of the main β-lactam resistance phenotypes and β-lactamase diversity identified in *Pseudomonas* spp. (including ESBLs of PER-, VEB-, BEL-, SHV-, TEM-, and OXA-types) (Table 6). In addition, most of those strains were resistant to carbapenems.

Susceptibility Testing

Susceptibility testing was performed using the Etest® (bioMérieux; La Balmes-les-Grottes, France) on Mueller-Hinton agar plates (Becton Dickinson, Le Pont de Chaix, France) at 37° C. and results were recorded according to US guidelines (CLSI), as updated in 2012. The breakpoints for imipenem, meropenem and doripenem are as follows; susceptibility (S)≤2, and resistance (R)≥8 μg/ml.

Carba NP Test

The Carba NP test was performed as previously detailed on strains grown on Mueller-Hinton agar plates (Becton Dickinson) at 37° C. for 18-22 h (7). This test is based on biochemical detection of the hydrolysis of the β-lactam ring of a carbapenem, imipenem, followed by color change of a pH indicator. Briefly, one calibrated dose (10 μl) of the tested strain directly recovered from the antibiogram was re-suspended in a Tris-HCl 20 mM lysis buffer (B-PER II, Bacterial Protein Extraction Reagent, Thermo Scientific, Pierce), vortexed for 1 min and further incubated at room temperature for 30 min. This bacterial suspension was centrifuged at 10,000×g at room temperature for 5 min. Thirty μl of the supernatant, corresponding to the enzymatic bacterial suspension, was mixed in a well of a 96 well tray with 100 μl of a 1 ml solution made of 3 mg of imipenem monohydrate (Sigma, Saint-Quentin-Fallavier, France) pH 7.8 phenol red solution and 0.1 mM $ZnSO_4$ (Merck Millipore, Guyancourt, France). Mixture of the phenol red solution and the enzymatic suspension being tested was incubated at 37° C. for a maximum of 2 h. Test results were interpreted by technicians who were blinded to the identity of the samples.

Results

Using the Carba NP test, the color of the wells turned from red to orange or yellow for all carbapenemase-producing isolates, with the exception of several GES-type producers that were not detected (Table 5). Wells corresponding to bacterial extracts of isolates that did not produce carbapenemase remained red (negative) whatever their level of carbapenem resistance was (Table 6). In most of the cases, a 30-min incubation time was sufficient for obtaining a frank color change for carbapenemase producers. The specificity and sensitivity of the test were found to be 100% and 94.4%, respectively. All tests were performed in triplicate, giving identical and reproducible results. Interestingly, a carbapenemase activity was detected in the two carbapenemase producers (IMP-1-producing *P. stutzeri* PB207 and *P. putida* NTU 92/99) that were basically susceptible to carbapenems according to the CLSI guidelines (Table 5).

The Carba NP test differentiated the carbapenemase producers (Table 5) from those isolates being carbapenem-resistant due to non-carbapenemase-mediated mechanisms such as combined mechanisms of resistance (outer-membrane permeability defect+/−associated with overproduction of cephalosporinase and/or ESBLs) (Table 6).

Discussion

As previously reported in Enterobacteriaceae (see example 2), the Carba NP test has multiple benefits for detecting carbapenemase activity in non fermenters such as in *Pseudomonas* spp. The Carba NP test eliminates the need of in-vivo detection of carbapenemase activity (Hodge test) and of β-lactamase inhibitor-based phenotypic techniques (boronic acid for KPC, EDTA for MBLs) that both require up to 24 to 72 h to be performed. In addition, inhibition of the β-lactamase activities are more difficult to evidence in *P. aeruginosa* than in Enterobacteriaceae due to the low outer-membrane permeability of *P. aeruginosa*. The use of such inhibition-based techniques may fail to detect carbapenemase activity even among true carbapenemase producers (Picao et al. Clin. Microbiol. 46:2028-2037). The Carba NP test clearly differentiates carbapenemase from non-carbapenemase producers among carbapenem-resistant *P. aeruginosa*. It may also detect carbapenemase activity among carbapenemase producers that remain carbapenem susceptible. The Carba NP test is the first technique available to identify carbapenemase producers with such high specificity, sensitivity, and rapidity (less than 2 h). However, the absence of detection of GES-type carbapenemases has to be considered, especially in geographical regions with high prevalence (i.e. Brazil, South Africa). This lack of detection of those specific GES derivatives may be due to their weak intrinsic carbapenemase activity. Indeed, GES-type carbapenemases are point-mutant analogues of GES-type ESBLs. They do not confer (in a wild-type *E. coli* background for example) a frank resistance to carbapenems ($k_{cat}/K_m$ range from 0.02 to 0.26 $M^{-1} \cdot s^{-1}$), as opposed for example to MBLs that confer a much higher level of carbapenemase resistance (usually $k_{cat}/K_m \geq 1$ $\mu M^{-1} \cdot s^{-1}$). In addition, the real clinical significance of the carbapenemase activity of GES-type variants as a source of in-vivo resistance to carbapenems (therapeutic failure) remained to be evaluated.

We have now routinely implemented the Carba NP test in our department. It has been used for searching carbapenemase activity among isolates with any slight decrease susceptibility to carbapenems among non fermenters. It has provided excellent and reproducible results. Results of this Carba NP test are used to select the strains for further testing by PCR and sequencing when a precise identification of the carbapenemase gene is needed.

Using this accurate test would be helpful for detecting patients infected or colonized with carbapenemase producers, which is of utmost importance for a better antibiotic stewardship and prevention of outbreaks. Use of the Carba NP test may be interesting in particularly for ICU and burn patients where multidrug-resistant *P. aeruginosa* are widespread. It offers a costless solution for detecting carbapenemase producers and preventing their spread, considering that they may harbor those carbapenemase genes onto plasmids that can spread. In addition, the control of carbapenemase-producing *Pseudomonas* spp. is important when considering that many of these carbapenemase genes are shared with Enterobacteriaceae. Noteworthy, the Carba NP test could also be used to implement a surveillance of carbapenemase-producing *Pseudomonas* spp. at worldwide scale.

TABLE 1

Thirty six carbapenemase producers of various enterobacterial species were studied by the method of the invention.

| | | | MICs (µg/ml) | | | Colorimetric |
| --- | --- | --- | --- | --- | --- | --- |
| | | Isolates | IMP | ERT | Acquired beta-lactamases | test |
| CARBAPENEMASES PRODUCERS | KPC | *E. cloacae* (1) | 4 | 6 | KPC-2 | + |
| | | *E. coli* PSP | 1 | 2 | KPC-2 | + |
| | | *E. coli* COL (2) | 4 | 0.5 | KPC-2 | + |
| | | *K. pneumoniae* H1516-6 COL (3) | 2 | 3 | KPC-2 + TEM-1 + CTXM-15 | + |
| | | *E. coli* DIN | 16 | >32 | KPC | + |
| | OXA-48 | *K. pneumoniae* BIC (4) | 0.5 | 2 | OXA-48 | + |
| | | *K. pneumoniae* CHA (5) | 0.5 | 1 | OXA-48 + TEM-1 | + |
| | | *K. pneumoniae* EGY | 2 | 3 | OXA-48 + CTX-M-15 | + |
| | | *K. pneumoniae* BEL | 1 | 4 | OXA-48 | + |
| | | *K. pneumoniae* RAM | 1 | 2 | OXA-48 | + |
| | | *E. cloacae* TUR (6) | 0.5 | 1 | OXA-48 + SHV-5 | + |
| | | *E. coli* HAN (7) | 0.5 | 1.5 | OXA-48 | + |
| | | *E. coli* BOU | 1 | 1.5 | OXA-48 + CTX-M-15 | + |
| | OXA-181 | *K. pneumoniae* OMA (8) | 0.5 | 2 | OXA-181 + CTXM-15 + OXA-1 | + |
| | | *K. pneumoniae* HOL | 0.5 | 1 | OXA-181 + CTX-M-15 | + |
| | | *P. rettgeri* RAP (9) | 1 | 2 | OXA-181 + OXA-1 | + |
| | NDM | *K. pneumoniae* UK (10) | 8 | 32 | NDM-1 + CTX-M-15 + CMY-4 + OXA-1 | + |
| | | *K. pneumoniae* 6759 GEN | 6 | 32 | NDM-1 + CTX-M-15 + OXA-1 + OXA-9 + OXA-10 + CMY16 | + |
| | | *K. pneumoniae* 1 OMA (11) | >32 | >32 | NDM-1 + CTX-M-15 + OXA-1 + OXA-9 | + |
| | | *K. pneumoniae* 2 OMA | >32 | >32 | NDM-1 + OXA-1 | + |
| | | *K. pneumoniae* 7 AFR | >32 | >32 | NDM-1 + OXA-1 + CTX-M-15 + CMY-6 + TEM-1 | + |
| | | *K. pneumoniae* IND | 6 | 8 | NDM-1 + OXA-1 + CTX-M-15 | + |
| | | *E. coli* 5649 GEN | 6 | 32 | NDM-1 + OXA-1 + CMY-30 + TEM-1 | + |
| | | *E. coli* RIC | 4 | 8 | NDM-1 + OXA-1 + OXA-10 + CMY-16 | + |
| | | *E. coli* 271 AUS (12) | 6 | 8 | NDM-1 + CTX-M-15 + TEM-1 | + |
| | | *E. coli* ALL | 4 | 8 | NDM-1 + OXA-1 + OXA-2 + CTX-M-15 + TEM-1 | + |
| | | *E. cloacae* IR38 | >32 | >32 | NDM-1 + CTX-M-15 | + |
| | | *P. stuartii* | >32 | >32 | NDM-1 + OXA-1 + CMY-6 | + |
| | | *C. freundii* STE (13) | >32 | >32 | NDM-1 + OXA-1 + OXA-9 + OXA-10 + CTX-M-15 + TEM-1 | + |
| | | *K. pneumoniae* SAB | 2 | 8 | NDM-1 | + |
| | | *K. pneumoniae* DIN | 8 | 32 | NDM-1 | + |
| | VIM | *E. coli* MAD (14) | 1.5 | 0.5 | VIM-1 + CTX-M-3 | + |
| | | *E. coli* DIH | 1 | 2 | VIM-19 | + |
| | | *K. pneumoniae* MAD | >32 | >32 | VIM-1 + CTX-M-3 | + |
| | IMP | *E. coli* MAD | 0.5 | 3 | IMP-1 | + |
| | | *K. pneumoniae* MAD (15) | 0.5 | 2 | IMP-13 | + |

MICs of imipenem (IMP) and ertapenem (ETP), acquired beta-lactamases and results of the colorimetric test are shown.
(**) Numbers in bold and in parenthesis correspond to the numbers in FIG. 1.

TABLE 2

Isolates with decreased susceptibility to carbapenems by non-carbapenemase based mechanisms or by producing non-carbapenemase broad spectrum β-lactamases were studied by the method of the invention.

| | | Isolates | MICs (µg/ml) IMP | ERT | Acquired beta-lactamases | Colorimetric test |
|---|---|---|---|---|---|---|
| NON-CARBAPENEMASE PRODUCERS | ESBL | K. pneumoniae (16) | 0.19 | 0.19 | CTX-M-15 | – |
| | | E. cloacae (17) | 0.19 | 0.19 | CTX-M-15 | – |
| | | E. coli FOR | 0.06 | 0.06 | CTX-M-15 | – |
| | | E. coli (18) | 0.06 | 0.06 | CTX-M-14 | – |
| | | E. cloacae 2185 | 0.19 | 0.19 | OXA-163 | – |
| | | K. pneumoniae 6299 (19) | 0.19 | 0.19 | OXA-163 | – |
| | | E. cloacae | 0.19 | 0.19 | VEB-1 | – |
| | | E. coli (20) | 0.06 | 0.06 | VEB-1 | – |
| | Plasmid mediated cephalosporinase | P. mirabilis | 0.19 | 0.19 | ACC-1 | – |
| | | E. coli (21) | 0.06 | 0.06 | ACC-1 | – |
| | | K. pneumoniae (22) | 0.19 | 0.19 | DHA-2 | – |
| | | E. coli Ec13 SYD (23) | 0.06 | 0.06 | CMY-2 | – |
| | | E. coli VMC (24) | 0.06 | 0.06 | CMY-10 | – |
| | Overexpression of chromosomal cephalosporinase | E. cloacae ARF (25) | 0.38 | 0.5 | AmpC | – |
| | | E. cloacae BLA | 0.38 | 0.5 | AmpC | – |
| | | E. cloacae CON (26) | 0.5 | 0.75 | AmpC | – |
| | Porin deficiency associated with ESBL | K. pneumoniae COO (27) | 0.5 | 0.75 | CTX-M-15 + SHV-28 | – |
| | | K. pneumoniae BER (28) | 0.5 | 0.75 | TEM | – |
| | Wild-type | E. coli J53 (29) | 0.06 | 0.06 | — | – |
| | | K. pneumoniae CIP53153 (30) | 0.19 | 0.19 | — | – |

MICs of imipenem (IMP) and ertapenem (ETP), acquired beta-lactamases and results of the colorimetric test are shown.
(**) Numbers in bold and in parenthesis correspond to the numbers in FIG. 1.

TABLE 3

Carbapenemase-producing clinical enterobacterial isolates submitted to the Carba NP test.

| Ambler class | Carbapenemase type | Species | β-lactamase | n | MICs range (mg/L) IMP | ERT | MER | Carba NP test |
|---|---|---|---|---|---|---|---|---|
| CLASS A | KPC-type | K. pneumoniae | KPC-2 | 27 | 0.5 to >32 | 4 to >32 | 1 to >32 | + |
| | | | KPC-3 | 3 | 0.5 to 8 | 4 to >32 | 1 to 8 | + |
| | | K. ozonae | KPC-3 | 1 | >32 | >32 | 2 | + |
| | | E. coli | KPC-2 | 5 | 0.5 to 4 | 0.5 to >32 | 0.5 to 2 | + |
| | | E. cloacae | KPC-2 | 7 | 1 to 24 | 1.5 to 32 | 0.75 to 16 | + |
| | | E. aerogenes | KPC-2 | 1 | 8 | >32 | 8 | + |
| | | C. freundii | KPC-2 | 2 | 8 to >32 | 1.5 to >32 | 1.5 to 3 | + |
| | | S. marcescens | KPC-2 | 2 | >32 | >32 | >32 | + |
| | | Salmonella spp. | KPC-2 | 1 | 4 | 1 | 0.25 | + |
| | NMC-A | E. cloacae | NMC-A | 1 | 16 | >32 | 16 | + |
| | SME-type | S. marcescens | SME-1 | 1 | 32 | 4 | 12 | + |
| | | | SME-2 | 1 | 32 | 4 | 12 | + |
| | GES-type | E. cloacae | GES-5 | 1 | >32 | >32 | >32 | + |
| | IMI-type | E. asburiae | IMI-2 | 1 | >32 | >32 | >32 | + |
| CLASS B | NDM-type | K. pneumoniae | NDM-1 | 16 | 0.5 to >32 | 2 to >32 | 1 to >32 | + |
| | | | NDM-4 | 1 | >32 | >32 | >32 | + |
| | | E. coli | NDM-1 | 7 | 1 to 16 | 3 to >32 | 1 to 16 | + |
| | | E. cloacae | NDM-1 | 1 | 2 | 16 | 2 | + |
| | | C. freundii | NDM-1 | 1 | >32 | >32 | >32 | + |
| | | P. stuartii | NDM-1 | 1 | 12 | 0.38 | 1.5 | + |
| | | P. rettgeri | NDM-1 | 1 | 3 | 0.5 | 1.5 | + |
| | VIM-type | K. pneumoniae | VIM-1 | 15 | 0.5 to >32 | 0.5 to >32 | 0.38 to >32 | + |
| | | | VIM-19 | 1 | 8 | 16 | 4 | + |
| | | E. coli | VIM-1 | 2 | 1.5 to 3 | 0.38 to 1.5 | 0.5 to 1 | + |
| | | | VIM-2 | 2 | 2 to 4 | 0.5 to 1.5 | 0.38 to 0.5 | + |
| | | | VIM-19 | 1 | 8 | 16 | 4 | + |
| | | E. cloacae | VIM-1 | 4 | 1 to >32 | 0.38 to >32 | 0.5 to >32 | + |
| | | S. marcescens | VIM-2 | 1 | >32 | >32 | >32 | + |
| | IMP-type | K. pneumoniae | IMP-1 | 5 | 0.5 to 8 | 2 to 4 | 1 to 8 | + |
| | | | IMP-8 | 2 | 0.5 to 1 | 0.5 to 1 | 0.5 | + |
| | | E. coli | IMP-1 | 2 | 0.5 | 3 to 4 | 0.5 to 1 | + |
| | | | IMP-8 | 1 | 6 | 8 | 3 | + |
| | | E. cloacae | IMP-1 | 12 | 8 to >32 | >32 | 2 to >32 | + |
| | | | IMP-8 | 2 | 0.75 to 1.5 | 0.5 to 1 | 0.5 to 1 | + |
| | | S. marcescens | IMP-1 | 2 | 8 to >32 | >32 | 2 to >32 | + |
| | | | IMP-11 | 1 | 8 | >32 | 2 | + |

TABLE 3-continued

Carbapenemase-producing clinical enterobacterial isolates submitted to the Carba NP test.

| Ambler class | Carbapenemase type | Species | β-lactamase | n | MICs range (mg/L) IMP | ERT | MER | Carba NP test |
|---|---|---|---|---|---|---|---|---|
| CLASS D | OXA-48 type | K. pneumoniae | OXA-48 | 15 | 0.38 to >32 | 0.38 to >32 | 0.38 to >32 | + |
| | | | OXA-181 | 2 | 0.5 to 1 | 2 to 4 | 0.5 to 1 | + |
| | | E. coli | OXA-48 | 6 | 0.38 to 3 | 0.5 to 16 | 0.12 to 1 | + |
| | | E. cloacae | OXA-48 | 3 | 0.5 to 1 | 0.5 to 16 | 0.5 to 1.5 | + |
| | | P. rettgeri | OXA-181 | 1 | 8 | 1 | 2 | + |

Range of minimum inhibition concentrations (MICs) of imipenem (IMP), ertapenem (ERT) and meropenem (MER) are shown, acquired carbapenemase as well as results of the Carba NP test. Carbapenemases are of KPC-type, NMC-A, SME-type, GES-type, IMI-type, NDM-type, VIM-type, IMP-type, and OXA-48 type.

TABLE 4

Non-carbapenemase producing clinical enterobacterial isolates submitted to the Carba NP test

| | Species | β-lactamase | n | MICs range (mg/L) IMP | ERT | MER | Carba NP test |
|---|---|---|---|---|---|---|---|
| ESBLs | K. pneumoniae | CTX-M-3 | 1 | 0.12 | 0.12 | 0.12 | − |
| | | CTX-M-14 | 1 | 0.12 | 0.12 | 0.12 | − |
| | | CTX-M-15 | 3 | 0.12 | 0.12 | 0.12 | − |
| | E. coli | CTX-M-1 | 1 | 0.12 | 0.12 | 0.12 | − |
| | | CTX-M-3 | 1 | 0.12 | 0.12 | 0.12 | − |
| | | CTX-M-14 | 2 | 0.12 | 0.12 | 0.12 | − |
| | | CTX-M-15 | 2 | 0.12 | 0.12 | 0.12 | − |
| | | VEB-1 | 1 | 0.12 to 0.25 | 0.12 | 0.12 | − |
| | E. cloacae | CTX-M-15 | 3 | 0.12 | 0.12 | 0.12 | − |
| | | VEB-1 | 1 | 0.12 | 0.12 | 0.12 | − |
| Plasmid mediated AmpC or Chromosomal AmpC + decreased membrane permeability | K. pneumoniae | DHA-1 | 1 | >32 | >32 | >32 | − |
| | | DHA-2 | 1 | 0.12 | 0.5 | 0.12 | − |
| | E. coli | Extended spectrum cephalosporinase | 1 | 0.12 | 0.12 | 0.12 | − |
| | | CMY-2 | 1 | 0.12 | 0.12 | 0.12 | − |
| | | CMY-10 | 1 | 0.12 | 0.38 | 0.12 | − |
| | | DHA-1 | 1 | 0.12 | 0.12 | 0.12 | − |
| | | ACC-1 | 1 | 0.12 | 0.12 | 0.12 | − |
| | | Overexpressed cephalosporinase | 1 | 16 | >32 | 2 | − |
| | P. mirabilis | ACC-1 | 1 | 0.25 | 0.12 | 0.12 | − |
| | E. cloacae | Overexpressed cephalosporinase | 7 | 0.12 to 16 | 1 to >32 | 0.12 to >32 | − |
| | E. aerogenes | Overexpressed cephalosporinase | 1 | 1 | 4 | 0.75 | − |
| | M. morganii | Overexpressed cephalosporinase | 2 | 1.5 to 2 | 0.12 | 0.5 | − |
| ESBL + decreased membrane permeability | K. pneumoniae | CTX-M-15 | 8 | 0.25 to 8 | 1 to >32 | 1 to >32 | − |
| | | SHV-28 | 1 | 1 | 4 | 1 | − |
| | | SHV-2a | 1 | 0.25 | 2 | 0.38 | − |
| | E. sakazaki | CTX-M-15 | 1 | 0.25 | 1.5 | 0.25 | − |
| | C. freundii | TEM-3 | 1 | 1 | 8 | 1 | − |

Range of minimum inhibition concentrations (MICs) of imipenem (IMP), ertapenem (ERT) and meropenem (MER) are shown, and results of the Rapid Carba test. β-lactamases are extended-spectrum β-lactamases (ESBLs), chromosomal and acquired plasmid-mediated cephalosporinase AmpCs.

TABLE 5

Detection of carbapenemase activity in carbapenemase producers using the Carba NP test

| Ambler Class | Carbapenemase type | Species | β-lactamase | MIC (μg/l) IMP | MER | Carba NP test |
|---|---|---|---|---|---|---|
| A | KPC | P. aeruginosa COL | KPC-2 | >32 | >32 | + |
| | | P. aeruginosa P13 | KPC-2 | >32 | >32 | + |
| | | P. aeruginosa PA-2 | KPC-2 | >32 | >32 | + |
| | | P. aeruginosa PA-3 | KPC-2 | >32 | >32 | + |
| | GES | P. aeruginosa GW-1 | GES-2 | 3 | 1 | − |
| | | P. aeruginosa P35 | GES-5 | >32 | >32 | − |
| B | VIM | P. aeruginosa P0510 | VIM-1 | >32 | >32 | + |
| | | P. fluorescens COU | VIM-2 | >32 | >32 | + |
| | | P. aeruginosa REZ | VIM-2 | >32 | >32 | + |
| | | P. putida 9335 | VIM-2 | >32 | >32 | + |

TABLE 5-continued

Detection of carbapenemase activity in carbapenemase producers using the Carba NP test

| Ambler Class | Carbapenemase type | Species | β-lactamase | MIC (μg/l) IMP | MER | Carba NP test |
|---|---|---|---|---|---|---|
| | | P. stutzeri P511503100 | VIM-2 | >32 | >32 | + |
| | | P. aeruginosa BY25753 | VIM-2 | >32 | >32 | + |
| | | P. aeruginosa V919005 | VIM-2 | >32 | >32 | + |
| | | P. aeruginosa AK5493 | VIM-2 | >32 | >32 | + |
| | | P. aeruginosa KA-209 | VIM-2 | >32 | >32 | + |
| | | P. putida NTU 91/99 | VIM-2 | >32 | >32 | + |
| | | P. aeruginosa CAS | VIM-4 | >32 | >32 | + |
| | | P. aeruginosa JAC | VIM-4 | >32 | >32 | + |
| | IMP | P. aeruginosa 12870 | IMP-1 | 12 | >32 | + |
| | | P. stutzeri PB207 | IMP-1 | 2 | 4 | + |
| | | P. putida NTU 92/99 | IMP-1 | 1 | 0.19 | + |
| | | P. aeruginosa | IMP-1 | >32 | >32 | + |
| | | P. aeruginosa 0607097 | IMP-2 | >32 | >32 | + |
| | | P. aeruginosa ITA | IMP-13 | >32 | >32 | + |
| | NDM | P. aeruginosa 453 | NDM-1 | >32 | >32 | + |
| | | P. aeruginosa 353 | NDM-1 | >32 | >32 | + |
| | GIM | P. aeruginosa 73-12198 | GIM-1 | 3 | 0.19 | + |
| | | P. aeruginosa 73-15574 | GIM-1 | >32 | >32 | + |
| | | P. aeruginosa 73-15553A | GIM-1 | >32 | >32 | + |
| | | P. aeruginosa 73-5674 | GIM-1 | >32 | >32 | + |
| | AIM | P. aeruginosa WCH2677 | AIM-1 | >32 | >32 | + |
| | | P. aeruginosa WCH2813 | AIM-1 | >32 | >32 | + |
| | | P. aeruginosa WCH2837 | AIM-1 | >32 | >32 | + |
| | SPM | P. aeruginosa 16 | SPM-1 | >32 | >32 | + |
| | DIM | P. stutzeri 13 | DIM-1 | >32 | >32 | + |
| | BIC | P. fluorescens | BIC-1 | >32 | 4 | + |

TABLE 6

Results of Carba NP test on non-carbapenemase producing Pseudomonas spp.

| Resistance mechanism | Species | Resistance determinants* | MIC (μg/l) IMP | MER | Carba NP test |
|---|---|---|---|---|---|
| Wild type | P. aeruginosa 76110 | none | 0.75 | 0.19 | — |
| | P. aeruginosa PU21 | none | 1.5 | 0.75 | — |
| | P. aeruginosa ATCC 27853 | none | 2 | 0.25 | — |
| | P. aeruginosa PA01 | none | 1 | 0.5 | — |
| | P. putida CIP 55-5 | none | 0.5 | 3 | — |
| AmpC over-production | P. aeruginosa 3-12 | overexpression of chromosomal AmpC | 3 | 0.25 | — |
| | P. aeruginosa VED | overexpression of chromosomal AmpC | 0.12 | 0.19 | — |
| Efflux | P. aeruginosa PA01 | Mex C/D-OprJ | >32 | 4 | — |
| | P. aeruginosa PT629 | Mex A/B-OprM | 1.5 | 1.5 | — |
| | P. aeruginosa PA01 | Mex X/Y-OprM | 1.5 | 0.75 | — |
| Porin deficiency | P. aeruginosa PA01 | OprM deficient | 0.75 | 0.5 | — |
| | P. aeruginosa H729 | OprD deficient | >32 | 6 | — |
| | P. aeruginosa Paeβ-02 | OprD deficient | 4 | 4 | — |
| | P. aeruginosa Paeβ-05 | OprD deficient | 16 | 8 | — |
| | P. aeruginosa Paeβ-30 | OprD deficient | 8 | 8 | — |
| | P. aeruginosa Paeβ-31 | OprD deficient | 16 | 8 | — |
| Porin deficiency + Efflux | P. aeruginosa Paeβ-19 | OprD deficient + MexA/B-OprM | 4 | 4 | — |
| | P. aeruginosa Paeβ-29 | OprD deficient + MexA/B-OprM + MexX/Y-OprM | 16 | 32 | — |
| | P. aeruginosa Paeβ-01 | OprD deficient + MexX/Y-OprM + MexC/D-OprJ | 4 | 8 | — |
| Porin deficiency + AmpC over-production | P. aeruginosa Paeβ-03 | OprD deficient + AmpC | 16 | 8 | — |
| | P. aeruginosa Paeβ-12 | OprD deficient + AmpC | 16 | 8 | — |
| | P. aeruginosa Paeβ-13 | OprD deficient + AmpC | 16 | 8 | — |
| | P. aeruginosa Paeβ-14 | OprD deficient + AmpC | 16 | 4 | — |
| | P. aeruginosa Paeβ-16 | OprD deficient + AmpC | 32 | 4 | — |

TABLE 6-continued

Results of Carba NP test on non-carbapenemase producing *Pseudomonas* spp.

| Resistance mechanism | Species | Resistance determinants* | MIC (μg/l) IMP | MER | Carba NP test |
|---|---|---|---|---|---|
| | *P. aeruginosa* Paeβ-23 | OprD deficient + AmpC | 32 | 16 | — |
| | *P. aeruginosa* Paeβ-25 | OprD deficient + AmpC | 8 | 8 | — |
| | *P. aeruginosa* Paeβ-26 | OprD deficient + AmpC | 4 | 4 | — |
| | *P. aeruginosa* Paeβ-32 | OprD deficient + AmpC | 64 | 16 | — |
| Porin deficiency + AmpC over-production + Efflux | *P. aeruginosa* Paeβ-04 | OprD deficient + AmpC + MexA/B-OprM | 16 | 16 | — |
| | *P. aeruginosa* Paeβ-24 | OprD deficient + AmpC + MexA/B-OprM | 32 | 32 | — |
| | *P. aeruginosa* Paeβ-28 | OprD deficient + AmpC + MexA/B-OprM | 16 | 4 | — |
| | *P. aeruginosa* Paeβ-15 | OprD deficient + AmpC + MexX/Y-OprM | 16 | 8 | — |
| | *P. aeruginosa* Paeβ-21 | OprD deficient + AmpC + MexX/Y-OprM | 16 | 32 | — |
| | *P. aeruginosa* Paeβ-22 | OprD deficient + AmpC + MexC/D-OprJ | 8 | 4 | — |
| | *P. aeruginosa* Paeβ-06 | OprD deficient + AmpC + MexX/Y-OprM + MexC/D-OprJ | 16 | 8 | — |
| | *P. aeruginosa* Paeβ-07 | OprD deficient + AmpC + MexX/Y-OprM + MexC/D-OprJ | 16 | 8 | — |
| | *P. aeruginosa* Paeβ-08 | OprD deficient + AmpC + MexX/Y-OprM + MexC/D-OprJ | 16 | 8 | — |
| | *P. aeruginosa* Paeβ-09 | OprD deficient + AmpC + MexX/Y-OprM + MexC/D-OprJ | 16 | 8 | — |
| | *P. aeruginosa* Paeβ-11 | OprD deficient + AmpC + MexX/Y-OprM + MexC/D-OprJ | 16 | 8 | — |
| | *P. aeruginosa* Paeβ-17 | OprD deficient + AmpC + MexX/Y-OprM + MexC/D-OprJ | 32 | 8 | — |
| | *P. aeruginosa* Paeβ-18 | OprD deficient + AmpC + MexA/B-OprM + MexX/Y-OprM | 64 | 64 | — |
| | *P. aeruginosa* Paeβ-27 | OprD deficient + AmpC + MexA/B-OprM + MexX/Y-OprM | 32 | 64 | — |
| | *P. aeruginosa* Paeβ-10 | OprD deficient + AmpC + MexA/B-OprM + MexC/D-OprJ | 16 | 8 | — |
| | *P. aeruginosa* Paeβ-20 | OprD deficient + AmpC + MexA/B-OprM + MexC/D-OprJ | 16 | 8 | — |
| ESBL | *P. aeruginosa* F6R7 | GES-1 | 1 | 0.75 | — |
| | *P. aeruginosa* DEJ | GES-9 | 2 | 1 | — |
| | *P. aeruginosa* RNL-1 | PER-1 | 6 | 6 | — |
| | *P. aeruginosa* A2O6 | PER-2 | 13 | 3 | — |
| | *P. aeruginosa* A5O6 | PER-8 | 1.5 | 0.38 | — |
| | *P. aeruginosa* A7O6 | PER-10 | 6 | 1 | — |
| | *P. aeruginosa* A3O6 | PER-11 | 3 | 1.5 | — |
| | *P. aeruginosa* A8O6 | PER-12 | >32 | 12 | — |

TABLE 6-continued

Results of Carba NP test on non-carbapenemase producing *Pseudomonas* spp.

| Resistance mechanism | Species | Resistance determinants* | MIC (µg/l) IMP | MER | Carba NP test |
|---|---|---|---|---|---|
| | *P. aeruginosa* A4O6 | PER-13 | 12 | 3 | — |
| | *P. aeruginosa* E3O6 | PER-19 | >32 | 12 | — |
| | *P. aeruginosa* E1O6 | PER-21 | 0.25 | 0.016 | — |
| | *P. aeruginosa* C2O7 | PER-26 | >32 | 8 | — |
| | *P. aeruginosa* C1O7 | PER-27 | >32 | >32 | — |
| | *P. aeruginosa* 15 | VEB-1 | 2 | 1.5 | — |
| | *P. aeruginosa* 51170 | BEL-1 | 1 | 0.5 | — |
| | *P. aeruginosa* 0602-52025 | SHV2a | 1.5 | 3 | — |
| | *P. aeruginosa* 1782 | SHV-5 | 2 | 2 | — |
| | *P. aeruginosa* SHAM | TEM-4 | 3 | 0.75 | — |
| | *P. aeruginosa* PU21 | OXA-2 | 2 | 1 | — |
| | *P. aeruginosa* PAO38 | OXA-4 | 0.016 | 0.19 | — |
| | *P. aeruginosa* PU 21 | OXA-10 | 2 | 1.5 | — |
| | *P. aeruginosa* PU 21 | OXA-11 | 3 | 1.5 | — |
| | *P. aeruginosa* NAJ | OXA-13 | 2 | 1.5 | — |
| | *P. aeruginosa* PU 21 | OXA-14 | 2 | 2 | — |
| | *P. aeruginosa* MUS | OXA-18 + OXA-20 | >32 | >32 | — |
| | *P. aeruginosa* ED | OXA-28 | 2 | 0.75 | — |
| | *P. aeruginosa* PIC | OXA-31 | >32 | 1.5 | — |
| | *P. aeruginosa* PG13 | OXA-32 | >32 | 12 | — |

*Underlined AmpC corresponds to overexpression of chromosomal AmpC OprD deficiency, AmpC overexpression and efflux system overproduction were previously characterized by qRT-PCR (12).

REFERENCES

Throughout this application, various references describe the state of the art to which this invention pertains. The disclosures of these references are hereby incorporated by reference into the present disclosure.

1. Queenan, A. M., and K. Bush. 2007. Carbapenemases: the versatile beta-lactamases. Clin. Microbiol. Rev. 20:440-458.
2. Nordmann, P., G. Cuzon, and T. Naas. 2009. The real threat of *Klebsiella pneumoniae* carbapenemase-producing bacteria. Lancet Infect. Dis. 9:228-236.
3. Poirel, L., J. D. Pitout, and P. Nordmann. 2007. Carbapenemases: molecular diversity and clinical consequences. Future Microbiol. 2:501-512.
4. Miriagou V, G. Cornaglia, M. Edelstein, I. Galani, C. G. Giske, M. Gniadkowski, E. Malamou-Lada, L. Martinez-Martinez, F. Navarro, P. Nordmann, L. Peixe, S. Pournaras, G. M. Rossolini, A. Tsakris, A. Vatopoulos, and R. Canton. 2010. Acquired carbapenemases in Gram-negative bacterial pathogens: detection and surveillance issues. Clin. Microbiol. Infect. 16:112-122
5. Carrër, A., L. Poirel, H. Eraksoy, A. A. Cagatay, S. Badur, and P. Nordmann. 2008. Spread of OXA-48-positive carbapenem-resistant *Klebsiella pneumoniae* isolates in Istanbul, Turkey. Antimicrob. Agents Chemother. 52:2950-2954.
6. Livermore D. M., and D. F. J. Brown. 2001. Detection of β-lactamase-mediated resistance. J. Antimicrob. Chemother. 48: suppl. 51, 59-64.
7. Bebrone C, C. Moali, F. Mahy, S. Rival, J.-D. Docquier, G.-M. Rossolini, J. Fastrez, R. F. Pratt, J.-M. Frere, and M. Galleni. 2001. CENTA as a chromogenic substrate for studying β-lactamases. Antimicrob. Agents Chemother. 45:1868-1871.
8. Massidda O., G. M. Rossolini, and G. Satta. 1991. The *Aeromonas hydrophila* cphA gene: molecular heterogeneity among class B metallo-β-lactamases. J. Bacteriol. 173:4611-4617.
9. Shannon K., and I. Phillips. 1980. β-Lactamase detection by three simple methods; intralactam, nitrocefin and acidimetric. J. Antimicrob. Chemother. 6:617-621.
10. Thomson, K. S. 2010. Extended-spectrum β-lactamase, AmpC and carbapenemase issues. J. Clin. Microbiol. 48:1019-1025.
11. Pluquet E., et al. 2011. A Sensitive and Specific Phenotypic Assay for Metallo-Beta-Lactamases Detection in Enteriobacteria using Moxalactal Disk Supplemented with EDTA (MOX-EDTA Disk Method), *J. Clin. Microbiol.*, published online ahead of print on May 4, 2011.
12. Walsh, T. R. et al. (2005) Metallo-beta-lactamases: the quiet before the storm? *Clin. Microbiol. Rev.* 18, 306-325
13. Franklin C., L. Liolios, and Y. Peleg. 2006. Phenotypic detection of carbapenem-susceptible metallo-β-lactamase-producing Gram-negative bacilli in the clinical laboratory. J. Clin. Microbiol. 44:3139-3140.
14. Kimura S., Y. Ishii, and K. Yamaguchi. 2005. Evaluation of dipicolonic acid for detection of IMP- or VIM-type metallo β-lactamase-producing *Pseudomonas aeruginosa* clinical isolates. Diagn. Microbiol. Infect. Dis. 53:241-244.
15. Migliavacca R., J.-D. Docquier, C. Mugnaioli, G. Amicosante, R. Daturi, K. Lee, G. M. Rossolini, L. Pagani. 2002. Simple microdilution test for detection of metallo-β-lactamase production in *Pseudomonas aeruginosa*. J. Clin. Microbiol. 40:4388-4390.
16. Giske et al. 2011. A sensitive and specific phenotypic assay for detection of metallo-β-lactamases and KPC in *Klebsiella pneumoniae* with the sued of meropenem disks supplemented with aminophenylboronic acid, dipicolinic acid and cloxacillin. Clin Microbiol Infect, 17: 552-556.
17. Livermore et al. 2011. Activities of NXL-104 combinations with ceftazidime and aztreonam against carbapenemase-producing Enterobacteriaceae. Antimicrob. Agents Chemother; 55; 390-394.
18. Clinical and Laboratory Standards Institute. 2010. Performance standards for antimicrobial susceptibility testing. CLSI M100-S20U. Update June 2010. Clinical and Laboratory Standards Institute, Wayne, Pa.

The invention claimed is:

1. A method for detecting the presence of carbapenemase-producing bacteria in a sample, said method comprising the steps of:
 a) performing cell lysis on a test sample in order to obtain an enzymatic suspension, wherein the cells in the test sample are not cultured in the presence of a carbapene and a pH indicator prior to step a);
 b) reacting a fraction of the enzymatic suspension obtained in step a) with
  a carbapenemase substrate selected from the group consisting of carbapenems and cephamycins, and
  a pH color indicator which will change color when the pH of the reaction mixture ranges from 6.4 to 8.4,
 wherein a color change after step b) indicates the presence of carbapenemase-producing bacteria in the test sample.

2. The method according to claim 1, wherein the test sample is a biological sample selected from the group consisting of a blood sample and a urine sample.

3. The method according to claim 1, wherein the carbapenemase-producing bacteria are of a genus selected from the group consisting of *Acinetobacter, Aeromonas, Bacillus, Bacteroides, Citrobacter, Enterobacter, Escherichia, Klebsiella, Morganella, Pandoreae, Proteus, Providencia, Pseudomonas, Ralstonia, Raoultella, Salmonella, Serratia, Shewanella, Shigella* and *Stenotrophomonas*.

4. The method according to claim 1, wherein the step of reacting b) is carried out in the presence of a carbapenemase activator selected from the group consisting of divalent cations, salts of divalent cations and mixtures of divalent cations and salts of divalent cations.

5. The method according to claim 1, wherein said step of reacting b) is carried out at a temperature ranges from 15° C. to 40° C.

6. The method according to claim 1, wherein the step of reacting b) is carried out over a period of time sufficient to observe a color change.

7. The method according to claim 1,
 wherein
  the carbapenemase substrate is imipenem, and
  the pH color indicator is phenol red,
  wherein the step of reacting b) is carried out in the presence of a carbapenemase activator which is zinc or salt a thereof,
 wherein a color change from red to yellow after step b) indicates the presence of carbapenemase-producing bacteria in the biological sample.

8. The method of claim 5, wherein the step of reacting b) is carried out at a temperature between 20° C. and 37° C. or at a temperature ranging from 35° C. to 37° C.

9. The method of claim 6, wherein the step of reacting b) is carried out over a period of time selected from the group consisting of: 5 to 120 minutes, 10 to 60 minutes, and 20 to 40 minutes.

10. The method of claim 1, wherein the carbapenem is selected from the group consisting of biapenem, ertapenem, doripenem, imipenem, meropenem, tebipenem and panipenem and the cephamycin is selected from the group consisting of moxalactam and cefoxitin.

11. The method of claim 1, wherein said method is carried out using a microtiter plate comprising a well or a series of wells comprising a carbapenemase substrate selected from the group consisting of carbapenems and cephamycins, and wherein said step of reacting b) includes the steps of
 adding the pH color indicator to the well or series of wells, and
 adding the fraction of the enzymatic suspension to the well or series of wells.

12. The method of claim 1, wherein said method is carried out using a reagent kit comprising a carbapenemase substrate selected from the group consisting of carbapenems and cephamycins and a pH color indicator.

13. A method for detecting the presence of carbapenemase-producing bacteria in a sample, said method comprising the steps of:
 a) performing cell lysis on a test sample in order to obtain an enzymatic suspension, wherein the cells in the test sample are not cultured in the presence of a carbapenem and a pH indicator prior to step a);
 b) reacting a fraction of the enzymatic suspension obtained in step a) with
  imipenem, and
  a pH color indicator which will change color when the pH of the reaction mixture ranges from 6.4 to 8.4,
 wherein a color change after step b) indicates the presence of carbapenemase-producing bacteria in the test sample.

* * * * *